US008657295B2

(12) United States Patent
Ashton-Miller et al.

(10) Patent No.: US 8,657,295 B2
(45) Date of Patent: Feb. 25, 2014

(54) DEVICE AND METHOD FOR MEASURING REACTION TIME

(75) Inventors: James A. Ashton-Miller, Ann Arbor, MI (US); Hogene Kim, Ann Arbor, MI (US); James T. Eckner, Ann Arbor, MI (US); James K. Richardson, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 117 days.

(21) Appl. No.: 12/815,619

(22) Filed: Jun. 15, 2010

(65) Prior Publication Data

US 2010/0324443 A1 Dec. 23, 2010

Related U.S. Application Data

(60) Provisional application No. 61/187,749, filed on Jun. 17, 2009.

(51) Int. Cl.
| A63B 67/00 | (2006.01) |
| A63B 71/00 | (2006.01) |
| A63F 9/00 | (2006.01) |
| A61B 19/00 | (2006.01) |
| A61B 5/117 | (2006.01) |
| A61B 5/103 | (2006.01) |
| G09B 19/00 | (2006.01) |

(52) U.S. Cl.
USPC ............................ 273/446; 600/587; 434/258

(58) Field of Classification Search
USPC .................. 600/587, 552–559; 473/422–436; 273/445–446
See application file for complete search history.

(56) References Cited

U.S. PATENT DOCUMENTS

| 1,730,726 | A | | 10/1929 | Goerke |
| 2,834,597 | A | | 5/1958 | Ylinen |
| 2,995,371 | A | | 8/1961 | Nelson |
| 3,334,424 | A | | 8/1967 | Pond |
| 3,545,749 | A | | 12/1970 | Schmued |
| 3,747,589 | A | | 7/1973 | Harrison et al. |
| 4,534,557 | A | * | 8/1985 | Bigelow et al. ............... 473/442 |
| 4,775,948 | A | | 10/1988 | Dial et al. |
| 5,526,326 | A | | 6/1996 | Fekete et al. |
| 5,912,864 | A | * | 6/1999 | Maurer ........................... 368/10 |
| 6,002,336 | A | * | 12/1999 | Widding et al. ............ 340/573.1 |
| 6,210,278 | B1 | * | 4/2001 | Klitsner ........................... 463/35 |
| 2005/0159679 | A1 | * | 7/2005 | Harbin et al. ................. 600/587 |

* cited by examiner

Primary Examiner — Brian Szmal
Assistant Examiner — Megan Leedy
(74) Attorney, Agent, or Firm — Harness, Dickey & Pierce, P.L.C.

(57) ABSTRACT

A manual neurological testing device for measuring a subject's reaction time comprising: a releasable holding member operable to be grasped by the subject; a stimulus device coupled with the releasable holding member, the stimulus device outputting a perceivable stimulus; and a measurement device coupled with the releasable holding member, the measurement device measuring the subject's reaction time for grasping the releasable holding member relative to the perceivable stimulus.

17 Claims, 4 Drawing Sheets

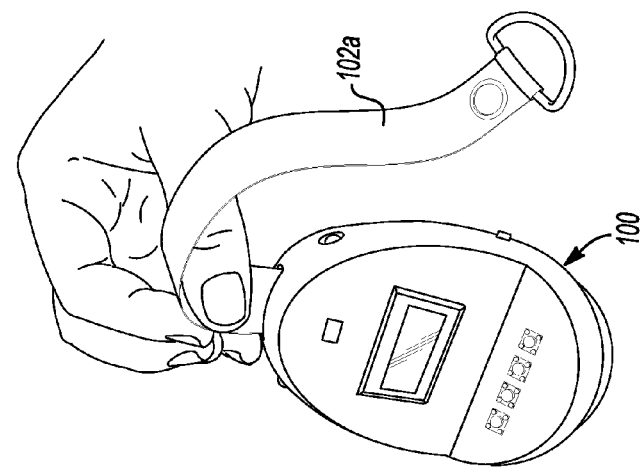
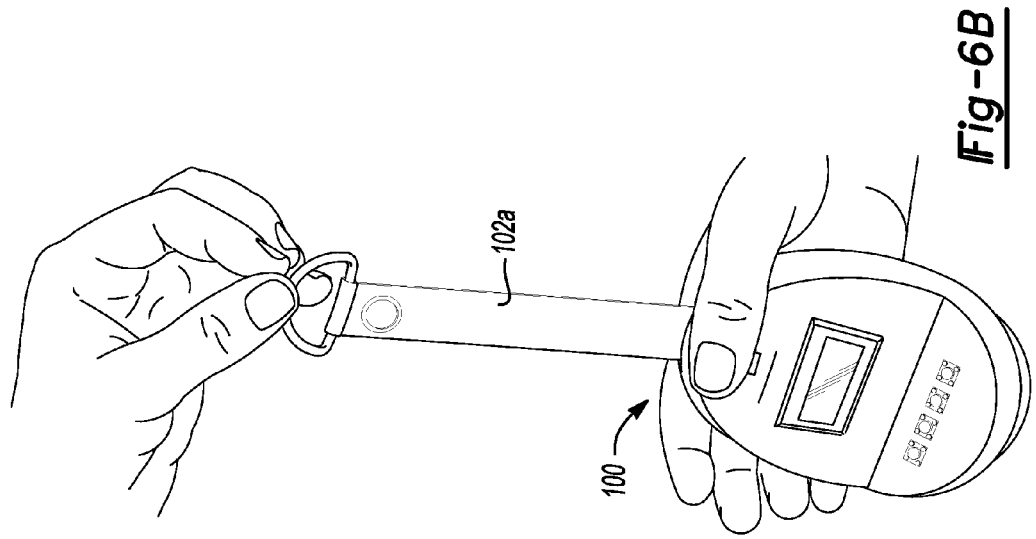

DEVICE AND METHOD FOR MEASURING REACTION TIME

CROSS-REFERENCE TO RELATED APPLICATIONS

This application claims the benefit of U.S. Provisional Application No. 61/187,749, filed on Jun. 17, 2009. The entire disclosure of the above application is incorporated herein by reference.

GOVERNMENT RIGHTS

This invention was made under Grant number AG024824 awarded by the National Institutes of Health. The government has certain rights in the invention.

FIELD

The present disclosure relates to a manual reaction time measuring device and methods for determining a subject's simple, recognition and choice reaction time.

BACKGROUND

This section provides background information related to the present disclosure which is not necessarily prior art.

Sport-related concussion is understood to be a significant public health concern which may be underreported. Studies have suggested that >5% of high school and college football players sustain a concussion during a single season. An athlete who has sustained an initial concussion is more susceptible to repeated concussions, and the athlete with multiple concussions is at increased risk for abnormalities in neuropsychological testing and ongoing symptoms. Premature return to play is of particular concern to society in general, and it appears to be associated with increased likelihood of further injury, prolonged experience of cognitive symptoms, and even death on rare occasions. The last concern refers to the "second impact syndrome", a catastrophic outcome in child and adolescent athletes.

Prolongation of reaction time after sports-related concussion has been recognized for many years. Importantly, concussed football athletes have shown impairments in reaction time as compared to controls several days after complete symptom resolution and clearance to return to play. However, present practice for determining reaction time typically includes a personal computer and specialized software-equipment not usually immediately available because of the associated cost (typically $500 per football team per year)— and is not available to the great majority of high school, and younger, athletes. This is especially important given evidence that the adolescent brain, as compared to that of the adult, is more vulnerable to sports-related concussion.

Reaction time can be partitioned into three intervals: a) Pre-motor time: from the onset of the stimulus to the onset of increased myoelectric activity in the response musculature; b) Electromechanical delay: from the depolarization of the response musculature to the acceleration of the response limb; and c) Movement time: from the initial acceleration of the response limb to completion of the task. A prolongation of any of these intervals can increase reaction time; e.g., a delay in upper extremity limb acceleration was the major source of delay in older women asked to move their hands quickly into position to break a fall. In some examples, a clinical reaction time can be defined as a measure of the speed with which a functional task relevant to sport, prevention of a blow to the head or face, is performed. However a clinical measure of reaction time would be of greatest use in evaluating sports-related concussion if it measures pre-motor events, since that interval includes central neurologic processing time.

Scientists define at least three types of reaction time including simple reaction time, recognition (or "Go/No Go") reaction time, and choice reaction time. Simple reaction time (SRT) is the reaction time obtained when the subject has to respond in a similar way to the same stimulus. In one example, one could obtain a simple reaction time by simply dropping an object at random intervals and asking the subject to catch it each time as quickly as possible. The time taken to catch the object from when it was dropped is the SRT. No decision-making is involved by the subject. Recognition reaction time (RRT) is the reaction time obtained when the subject recognizes the presence/absence of a stimulus at the time the object is dropped and takes the appropriate action as quickly as possible. So in one example, the subject will have been asked to catch the object that is dropped using a pinch grip if a light comes on, but to let it drop if the light does not come on. Here the stimulus to catch the object occurs only intermittently and a decision has to be made as to whether to catch it or not. Choice reaction time (CRT) is the reaction time obtained when the subject interprets the stimulus that is presented at the time the object is dropped so as to make one of at least two different responses as quickly as possible. An example would be that the subject is asked to catch the object when it is dropped using their thumb and first finger if the light is green, but with their thumb and third finger if it is red. Here the stimulus varies, every trial and subject is burdened with making the choice between the two different motor responses or catching actions when responding to the stimulus as quickly as possible. It is known that the reaction time (RT) increases as a function of the number of choices according to the formula $RT = a + b\ \log_2(n+1)$, where a and b are constants representing the intercept and slope of the function, and n is the number of choices.

Therefore an inexpensive clinical measure of reaction time would be welcomed in the evaluation of sports- and age-related neurological disorders or conditions, including sports-related concussion. Moreover, such a measure would be of even greater use if it was found to predict a sports-related protective reaction time (SPRT). The immediate availability of this information could influence return to play decision-making, and prevent repeat sports-related concussion or other injury.

SUMMARY

This section provides a general summary of the disclosure, and is not a comprehensive disclosure of its full scope or all of its features.

The present disclosure provides in exemplary aspects, a manual neurological testing device for measuring a subject's reaction time. In some embodiments, the device comprises a releasable holding member operable to be grasped by the subject; a stimuli output device coupled to the releasable holding member, the stimuli output device outputting a perceivable stimulus; and a measurement device coupled to the releasable holding member. The measurement device can be configured to measure the subject's reaction time for grasping the releasable holding member relative to the perceivable stimulus.

In other exemplary aspects, the present disclosure also provides a method for manually measuring the reaction time in a subject, the method comprising: (a) positioning a manual neurological testing device within grasp of the subject, operable to measure the reaction time of subject, said manual testing device having a releasable holding member operable to be grasped by the subject; a stimuli output device coupled with the releasable holding member, the stimuli output device outputting a perceivable stimulus; and a measurement device coupled with the releasable holding member; (b) releasing the holding member with or without the perceivable stimulus; and (c) determining the time taken for the subject to grasp the releasable holding member after releasing the releasable holding member.

In a further aspect of the present disclosure, the perceivable stimulus can include a visual stimulus, for example, an off or on light, one or more colored lights, for example, a red light and a green light. Other perceivable stimuli can include one or more sounds, music or alerts similarly used to register an on-off stimuli and also recognition stimuli where one sound indicates to the subject to grab the testing device and a different sound indicates not to grab the testing device.

The manual neurological testing device offers several advantages over computer-based methods including face validity—intrinsically motivating subjects to exert significant effort to react because it replicates a time-critical situation we are all used to having to respond to—catching a fragile object that falls off a table before it strikes the ground, thus an excellent measure of reaction time.

Motivation is an important factor to consider when measuring reaction time in a clinical setting because of its effect on subject performance. Current methods of accurately measuring recognition or choice reaction time require a computer with specialized software. These computer-based methods fail to provide the same physical level of motivation because the physical stimulus is not a sudden movement of a physical body that has to be physically caught as soon as possible (rather a key has to usually be depressed on a computer keyboard according to a sense of urgency that is entirely reliant on the testee self-generating, not imposed upon him or her by the laws of physics of a falling body). The present device is also more motivating than computer testing to determine reaction times because the present testing device imposes the sense of urgency upon the testee while providing instant dissemination of results to both the subject and the examiner. The present method can be well controlled and results in higher reproducibility than computerized testing.

The portability and simplicity of the manual neurological testing device renders the device better suited for routine clinical use than computerized assessment methods. Other uses of the manual neurological testing device can include monitoring medication effects, establishing fall risk, return to driving testing, the effects of sleep apnea, dementia screening, return to work in hazardous occupations testing and sobriety testing, as well as evaluating symptoms from many conditions to be specified later.

The device has an order of magnitude lower cost than a computerized PC-based testing system. It can be made for less than $50. This puts the devices of the present technologies in a price range that every professional team, college, high-school, middle school and elementary school and would be able to afford for their football, basketball, lacrosse, field hockey, baseball, softball, soccer, gymnastics, and ice hockey teams as well as participants of martial arts, teams that are exposed to the danger of a concussion every time they participate. The same is true for military medics needing to test or evaluate military personnel who have been exposed to concussion from the detonation of nearby explosive devices.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows a block diagram of the signal paths between various components used in an exemplary manual neurological testing device in accordance with the present disclosure.

FIG. 2 is a photograph of a partial view of the manual neurological testing device with the subject's hand in position at, but not touching, the spacer portion of the holding member ready to react to a stimulus and grasp the manual neurological testing device in accordance with the present disclosure. The inset shows a photograph of the front view of the distal portion of the manual neurological testing device. A digital clock and display is shown indicating a reaction time result in milliseconds.

FIG. 6B is a photograph of the illustrative example of the manual neurological testing device of FIG. 6A in a pre-release position.

FIG. 6C is a photograph of the illustrative example of the manual neurological testing device of FIG. 6A in a caught position.

Corresponding reference numerals indicate corresponding parts throughout the several views of the drawings.

DETAILED DESCRIPTION

Figure 1:
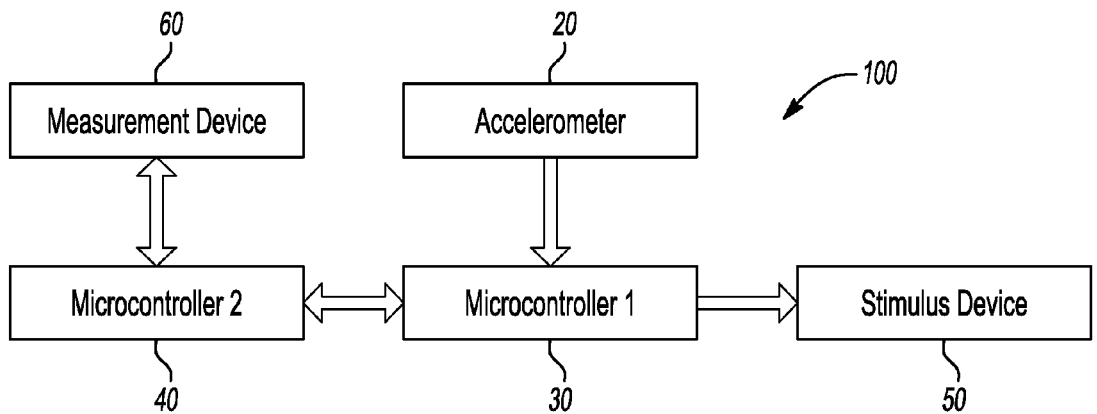

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present disclosure provides a manual testing neurological device that when used in a controlled neurological procedure is capable of quickly and accurately measuring human reaction time.

Manual Neurological Testing Device

As used herein, the term "manual" can include devices that can be released by the clinician and grasped by the subject using any part of the human body, including for example, the hand, knees, legs, arms, elbows, feet and the like. The body part can also be on the dominant side or the non-dominant side, or both. Hence, contacting a mouse, keyboard key, or computer display to measure reaction time is not contemplated in the present disclosure.

In some exemplary embodiments as illustrated in FIGS. 1-6C, the manual neurological testing device 100 (herein referred to as the "testing device 100") can include: a) a releasable holding member 102 operable to be grasped by the subject; b) a stimuli output device 50 coupled with the releasable holding member 102, the stimuli output device 50 outputs a perceivable stimulus to the subject; and c) a measurement device 60 coupled with the releasable holding member 102, the measurement device measures the subject's reaction time for grasping the releasable holding member 102 relative to the perceivable stimulus.

Figure 2:
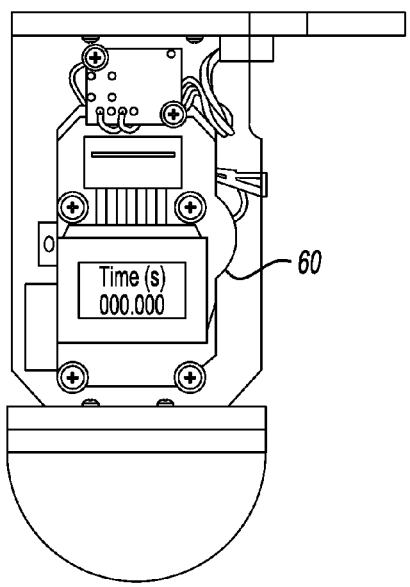
Figure 2:
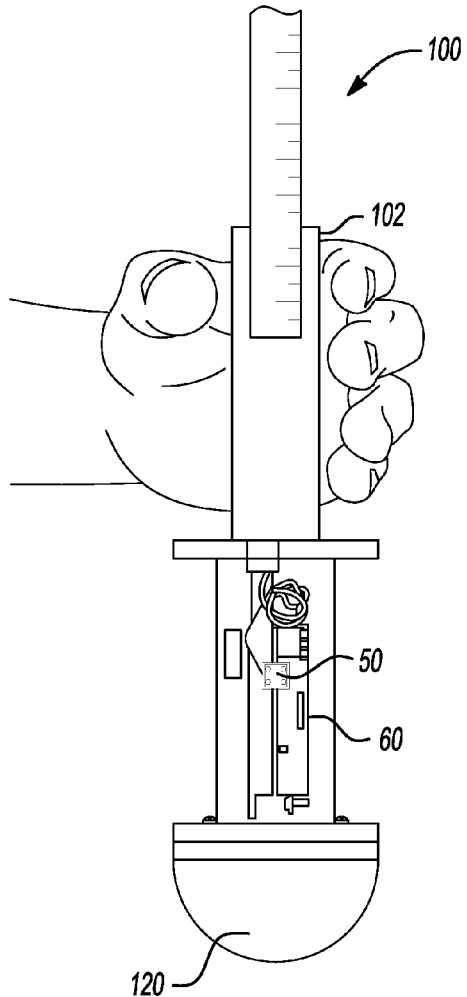
Figures 5, 6A:
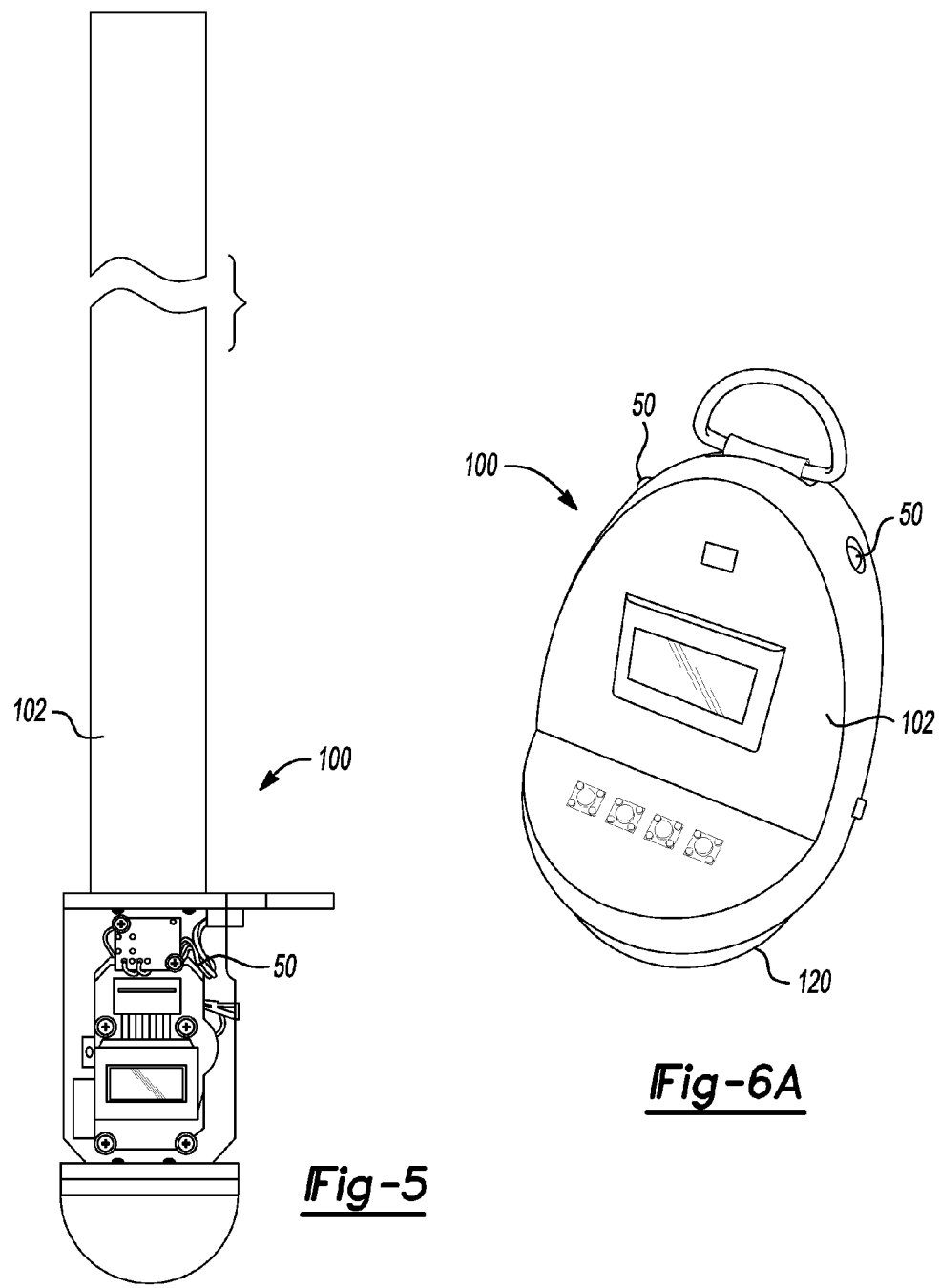
FIG. 5 is a photograph of an illustrative example of a manual neurological testing device having a biconcave holding member in accordance with the present disclosure.
FIG. 6A is a photograph of an illustrative example of a manual neurological testing device in accordance with the present disclosure.

In some embodiments the present disclosure, testing device 100 includes a holding member 102 that can serve as a structural component of the testing device 100 to mount the various components as shown in FIGS. 2 and 5. The holding member 102 can be elongated, measuring from about 20 cm to about 200 cm. The holding member 102 can be configured to be grasped by the subject's hand during the testing procedure as shown in FIGS. 2 and 6C. While the overall geometry of the holding member 102 can be varied, depending on the subject being tested, the holding member 102 can illustratively have a cross-section shaped like an hour-glass or biconcave, a rectangular shape having circular segments completing the ends, circular, triangular, square, rectangular and oval. In some embodiments, the biconcave shape of the holding member 102 cross-section promotes reproducible pinch grip grasping movements. The biconcave shape of the holding member 102 also facilitates the subject to use a pinch grip rather than a palm grip to actually grasp or catch the device. This reduces the time needed for the subject's fingers to close onto the surface of the device.

In some embodiments, the holding member 102 can be configured to have a range of lengths and cross-section widths, i.e. at the center of the concave surface, for example from about 0.5 cm to about 10 cm to accommodate varying subject hand sizes (i.e. juvenile, adolescent and adult). The holding member 102 can be manufactured from any solid material including plastic, polymer, metal, wood, ceramic, glass and combinations thereof. In some embodiments, the holding member 102 can be made from a dense plastic material.

Figure 3:
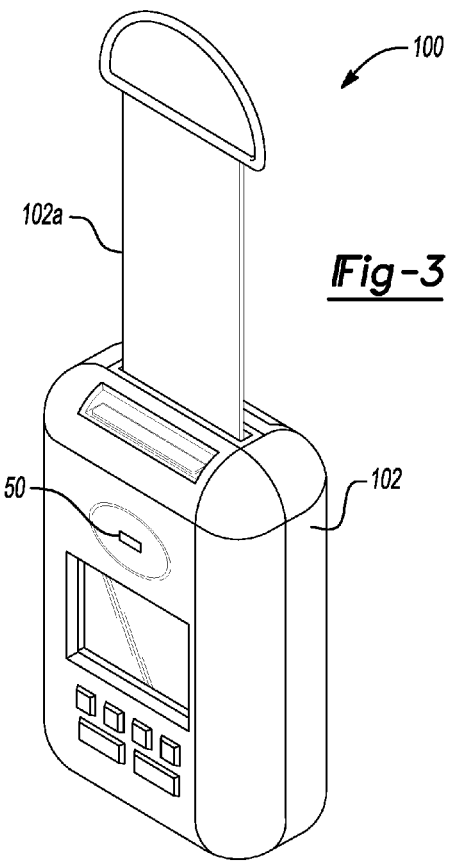
FIG. 3 shows a schematic illustration of the portable manual neurological testing device and a retractable leash holding member in accordance with the present disclosure.

In some embodiments, the testing device 100 can include the components shown in FIG. 1 attached to a retractable or pivotable holding member 102. With reference to FIGS. 1 and 3, the accelerometer 20, microcontrollers 30 and/or 40, stimulus device 50 and measurement device 60 can be incorporated into a unitary device shown in FIG. 3 having the size relative to a cell phone or even as small as a key fob. The unitary testing device 100 is attached to a holding member 102 shown in FIG. 3 as a retractable leash and can measure from about 20 cm to about 100 cm. Alternatively, the holding member 102 may be designed to telescope, in the manner of a radio antenna, be foldable in the manner of a segmented tent post whose disassembled parts are held together by a thin bungee cord, and pivotable or hinged pole segments much like a carpenter's ruler. As shown in FIG. 3, the testing device 100 can be made to be compact by replacing the elongated solid holding member 102 with a flexible structure 102a such as a woven nylon tape that is retracted on a take-up spool inside the device when not in use. The tape can have a cross-section that is like that of a ribbon or like that of a closed tube or stocking for increased resistance to rotation.

In some embodiments, the testing device 100 can also provide added functionality, such as being able to automatically score the recognition or choice reaction time response accuracy (i.e., the percentage of trials wherein the subject only catches the testing device 100 when the LED lights, but correctly allows it to fall when the LED does not light upon the device being released by the clinician, recognition, or catches the testing device 100 using their thumb and index finger when the LED is green and their thumb and middle finger when the LED is red, choice). Additional optoelectronic, wireless and infra red sensors, diodes and adapters contained within the unitary testing device 100 for receipt and transmission of various data and other programmable instructions to and from the device are contemplated. The testing device 100 can also provide the means to store reaction time performance results made at an earlier time, or baseline, so that they may be rapidly compared with the results of tests made at a later time, or follow up.

Figure 4:
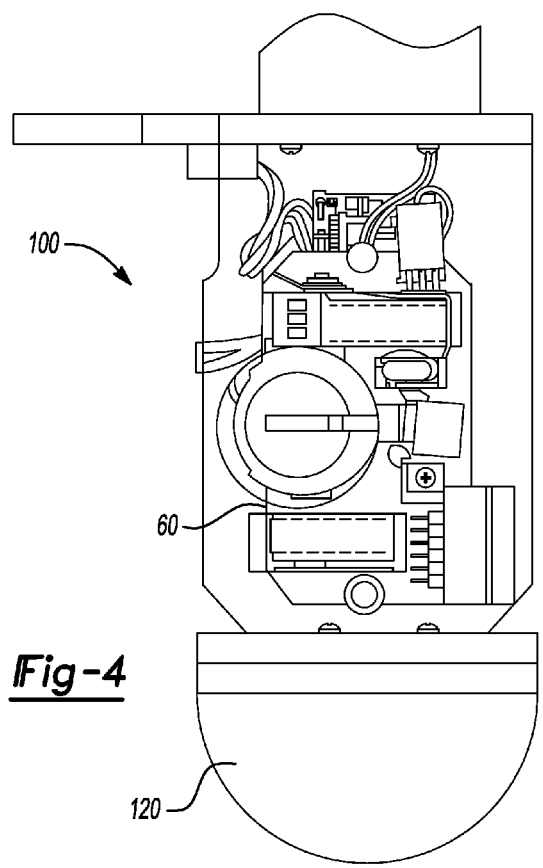
FIG. 4 is a photograph of the rear side of the distal portion of the manual neurological testing device showing the various components described in FIG. 1.

In some embodiments, the holding member 102 can be fitted with various components that permit the measurement and determination of the subject's reaction time, including simple reaction time and recognition reaction time. As shown in FIG. 1, an exemplary testing device 100 can include an accelerometer 20, one or more of microcontrollers 30 and 40, stimulus device 50 and a measurement device 60. FIGS. 2, 4 and 5 show a holding member 102 having the accelerometer 20, microcontrollers 30 and 40, stimulus device 50 and measurement device 60 located at the distal end of the testing device 100. Best illustrated in FIG. 2, the holding member 102 can include a region called a spacer 50. The spacer 50 maintains the subject's distal digits a fixed distance apart so that the fingers must travel a uniform distance before they touch the holding member 102 after release. The spacer 50 can be shaped differently to the rest of the holding member 102 or may be similarly shaped.

In some embodiments, the testing device 100 can include an accelerometer 20 that is integrated and coupled with the testing device 100 to sense movement of the testing device 100 after it has been released by the clinician, i.e. the accelerometer 20 can measure the onset and offset of motion of the testing device 100. The accelerometer 20 can be any linear accelerometer capable of sending a signal to at least one of the microcontrollers 30 and 40 when it senses both onset and offset of motion. The accelerometer 20 is an illustrative example of a displacement sensor, other displacement sensors known in the art can also be used to detect onset of acceleration and deceleration of the testing device 100 when released by the clinician, and caught by the subject respectively. An accelerometer 20 useful in the present disclosure can include the Model ADXL202 accelerometer manufactured by Analog Devices, Inc. Norwood, Mass.

In some embodiments, the testing device 100 can include a displacement-measuring device that is not integrated or coupled with the testing device 100 but is disposed at a remote location to sense movement of the testing device 100 after it has been released by the clinician, i.e. the accelerometer or displacement-measuring device can measure the onset and offset of motion of the testing device 100 remotely. The displacement-measuring device can be any optoelectronic sensor capable of sensing both onset and offset of motion. An example of such a displacement measuring sensor would be a Northern Digital Inc., Certus system or any video-based motion capture system such as the VICON system. The sensor would then send a signal to at least one of the microcontrollers 30 and 40 to signal the onset and offset of motion.

In some embodiments, the testing device 100 also includes at least one microcontroller, illustratively shown in FIG. 1 as microcontroller 30 and microcontroller 40. Microcontrollers 30 and/or 40 can be configured to perform a variety of functions including: determine the test mode program (simple reaction time or "Go-No-Go" recognition reaction time), measure the onset of acceleration of the testing device 100, send a signal to a stimulus device 50 upon determining a threshold acceleration, send a signal to a stimulus device 50 to activate one of two different stimuli from stimulus device 50, senses a significant deceleration signal from the accelerometer 20 as when the testing device 100 is grasped by the subject and send a signal to stop the measurement device 60. The microcontrollers 30 and 40 can include RISC type of microcontrollers, commercially available as Model PIC16F84A manufactured by Microchip Technology Inc., Chandler, Az., USA.

The testing device 100 of the present disclosure can further comprise a measurement device 60 that can be used to ultimately measure and determine the subject's reaction time. Moreover, in some embodiments, measurement device 60 can be used for determining response accuracy. The measurement device 60 can be automated and in data and electronic communication with the microcontrollers 30 and/or 40 or the measurement device 60 can be a ruler. In some embodiments, the measurement device 60 can include a digital time recording device that is programmable and/or that is in electrical communication with at least one of the microcontrollers 30 and 40 and is capable of reporting the elapsed time measured from the onset of acceleration and stimulus delivery to the time the testing device 100 has been grasped by the subject. In some embodiments, the measurement device 60 can include a crystal oscillator. Although many crystal oscillators would be suitable for use in the present disclosure, one such exemplary oscillator can include Model HC49US (4.096 MHz) manufactured by Citizen Holdings Co., LTD., Tokyo, JP. A microcontroller similar to that mentioned above can be arranged to count pulses from the oscillator and transfer the number to a second microcontroller which controls an LCD display unit so as to display a number—the reaction time in, say, units of msec. An LCD display useful in the present disclosure can include the Model MDL(S)-82603 manufactured by Varitronix LTD, Kwun Tong, Hong Kong. In some embodiments, the measurement device 60 can work in concert with microcontrollers 30 and 40 to determine and report the number of correct (incorrect) response in the Recognition Reaction Time test.

As noted above, the measurement device 60 can include a set of ruler markings imprinted on the holding member 102 operable to indicate the distance the testing device 100 has moved since the testing device 100 has been released and before it was caught. The ruler markings can be marked in millimeters and the holding member 102 can have a roughened surface to prevent slippage between the member and fingers when it is caught by the test subject. The measurement device 60 can include the digital clock and/or the ruler markings. In some embodiments the ruler markings can represent the elapsed time the member has been in free-fall (in ms) since release rather than using metric measure for conversion to time.

In some embodiments, the reaction time testing device 100 of the present disclosure requires the use of a perceivable stimulus to indicate to the subject, upon the release of the holding member 102 by the examiner, to resist catching the testing device 100 or to catch the testing device 100. The stimulus device 50 produces a stimulus that is perceivable to the subject. The stimulus itself is not limited to any one physical form. In some embodiments, the stimulus device 50 outputs a perceivable stimulus detectable by the subject. The perceivable stimulus can include a single light, for example, as produced from a single LED that when turned on signals to the subject that the released testing device 100 is to be caught. If the LED is not turned on, and the testing device 100 is released then the subject is meant to let the testing device 100 fall to the ground. This type of testing method is designed to test and measure the recognition reaction time of the subject. Alternatively, for choice reaction time determination, the stimulus device 50 must be capable of outputting at least two different perceivable stimuli. In some embodiments, the stimulus device 50 can be a single LED that is capable of displaying, for example, two different colors, two different light intensities, two different light frequencies, for example, one continuous light and one light that flickers repetitively, or strobe. Alternatively, the stimulus device 50 can include two or more LEDs, each operable for providing a perceivable stimulus that are different to the other. In some embodiments, the stimulus device 50 can also output a perceivable stimulus that is not visual, but rather aural. As with the description of LEDs, the aural signal generator can be a single sound generator or a multi-sound generator, since the sounds may be perceived by the subject as an indicator of whether to grasp the testing device 100 after being released or whether to let the testing device 100 fall. Alternatively, the stimulus device could trigger (wirelessly) a tactile (vibratory) (sensory) feedback at two or more locations on the skin.

In some embodiments, the testing device 100 can have an optional output device that electronically displays the subject's reaction time. The output device can be integrated with the measurement device and display the subject's reaction time as shown in FIG. 2 (inset).

In some embodiments, the testing device 100 can have a weight 120 or other stabilizing device such as a weighted ballast. The weighted ballast 120 can be attached to the lower end or distal portion of the holding member 102 to increase its inertia as a pendulum thereby helping to maintain the device in a vertical position prior to being released. In other embodiments, the various components described in FIG. 1 can serve as the weight to help maintain the testing device 100 in a vertical position without the need for a weighted ballast 120.

The testing device 100 can include: a) a releasable elongated holding member 102 configured to be grasped by the subject; b) a control module coupled with the releasable elongated holding member 102, the control member comprising: i) a displacement sensor operable to determine a predetermined onset and an offset of motion of the releasable elongated holding member 102 in a vertical direction; ii) a controller connected to the displacement sensor, the controller comprising: a stimulus driving output and a timer on/off output; and iii) a timing device in communication with the timer on/off output, the timing device measures the period of time elapsed between the predetermined onset and the offset of motion of the releasable elongated holding member 102, the timing device sends the period of time elapsed to the controller; and c) a stimuli output device coupled with the releasable elongated holding member 102 to be perceived by the subject, the stimuli output device being in electronic communication with the controller and is operable to output a stimulus in response to the stimulus driving output.

Methods for Determining a Subject's Reaction Time

The above described testing device 100 can be employed to determine at least three patterns of reaction time that provide valuable neurological information as to the condition or status of the subject being tested. These at least three reaction times can include simple reaction time, recognition reaction time, and choice reaction time.

In some embodiments, a method for determining the subject's simple, recognition and/or choice reaction time can include: positioning a neurological manual testing device 100 within the grasp of the subject. The manual testing device 100 can have a releasable holding member 102 which is configured to be grasped by the subject and a stimuli output device which can be coupled with the releasable holding member 102. The stimuli output device is capable of outputting a perceivable stimulus. The testing device 100 also includes a measurement device which can be coupled with the releasable holding member 102. The holding member 102 is then released with or without the perceivable stimulus; and the time taken for the subject to grasp the releasable holding member 102 in a specified manner after being releasing is measured.

In some embodiments, a method to determine a simple reaction time of a subject is provided. Generally, the subject being tested can be positioned sitting in an upright position with their dominant or non-dominant forearm resting on a horizontal surface such that their hypothenar eminence is positioned at the edge of the surface. The clinician or examiner can suspend the device vertically with the holding member 102 spacer region near and the hand and horizontal surface on which the subject's forearm is resting. Subjects can hold their dominant or non-dominant hand open around the "spacer" portion of the device as shown in FIG. 2 such that their first and second digits are close to, but not touching the spacer in a pinch grip.

To determine a simple reaction time, subjects can be instructed to direct and maintain their gaze at the light-emitting diode shown on the top left hand corner of FIG. 4 and, when the testing device 100 is released, to catch the device as quickly as possible after its release. Direction of gaze is specified because it is understood that the threshold for the subject to visually detect the onset of the release of the testing device 100 is better when using foveal vision that when using peripheral vision: in the former case it is on the order of 0.017 to 0.033 deg/sec as an angular velocity subtended at the retina. At pre-determined random time intervals, the examiner releases the device and the subject catches it as quickly as possible. For an electronic readout, the device measures reaction time internally via an accelerometer and displays the reaction time in milliseconds on a digital output screen.

To determine a recognition reaction time measured as a "Go or No-Go" paradigm, the method for the above simple reaction time determination method is slightly modified. In an exemplary method for determining a recognition reaction time, the subject can also be positioned sitting in an upright position with their forearm resting on a horizontal surface such that their hypothenar eminence is positioned at the edge of the surface. The clinician or examiner can suspend the testing device 100 vertically with the holding member 102 near the hand and horizontal surface on which the subject's forearm is resting. Subjects hold their hand open around the "spacer" portion of the device as shown in FIG. 2 such that their first and second digits are close to, but not touching the spacer in a pinch grip.

To determine recognition reaction time, subjects can be instructed to direct their attention to the stimulus device 50, for example, a colored light from a light source attached to the testing device 100, such as a light-emitting diode (LED) or an audible stimulus from a speaker attached to the testing device 100. In some embodiments, the subject can direct and maintain their gaze at the stimulus device 50 if it is a visible stimulus. To measure the reaction time, the testing device 100 is released by the clinician and if the stimulus device 50, for example, having a LED on the testing device 100 illuminates contemporaneously as the device is released, the subject catches the device as quickly as possible. If the LED does not illuminate, the subject allows the device to fall to the ground without catching it. At pre-determined random time intervals, the clinician releases the device and the subject catches it as quickly as possible when the test condition is satisfied. In some embodiments circuitry connected to stimulus device 50 can either randomize whether the LED stimulus is illuminated on a trial or presents a pre-recorded test sequence. For an electronic readout, the testing device 100 measures reaction time internally via an accelerometer and temporal recording device and displays the reaction time in milliseconds on a digital output screen. It should be appreciated that other stimulus can be used.

In some embodiments, the spacer can have two or more proximity sensors 100 (see FIGS. 6A-6C), each for example consisting of an infrared emitter and detector pair connected to some circuitry, located on opposing surfaces of the spacer, that sense whether distances to the finger on one side of the space and the thumb on the other side of the spacer are within tolerance: in other words neither touching the spacer directly nor being so far away that the time required by the subject to move the fingers through that distance materially affects the measured reaction time needed to catch the device. When the distance from the spacer is within tolerance, a signaling device can be used to transmit that information to the examiner thereby indicating that conditions are right to be able to release the device when he/she so chooses. An example of a suitable proximity sensor is the Osram SFH 7741 short range proximity sensor.

In some embodiments, the measurement device 60 disposed on the testing device 100 can consist of markings approximating a ruler that can be used to measure the distance the testing device 100 has traveled towards the ground before it has been grasped. In the "ruler" method, the top of the subject's finger or hand when held close to the spacer region of the holding member 102 as shown in FIG. 2 is noted and read from the rule as the initial measurement point. Then the device is released and grasped as appropriately indicated by the stimulus device 50. Then, the top of the same subject's finger or hand grasping the testing device 100 is measured on the ruler and is noted as the final measurement point of the ruler. The difference between the first and second measurement points is therefore the distance the holding member 102 has traveled. The resting position of the subject's hand after the device has been grasped can be used to determine the delta, i.e. the distance the testing device 100 has traveled. This distance can be used to calculate the reaction time of the subject. The reaction time as measured by the "ruler" method is the square root of twice the distance traveled in meters divided by the acceleration caused by gravity on the Earth of 9.8 m/s$^2$. So for example, if the subject were to let the testing device 100 fall 8.0 cm after receiving the appropriate stimulus to grasp the falling testing device 100, the reaction time can be calculated as the square root of (two times 0.08 m divided by 9.8) which is 0.1278 seconds or approximately 128 milliseconds. Or in other embodiments the markings could be in ms instead of mm, with the above calculation already performed to determine the location of the markings in the first place.

To determine choice reaction time, subjects can be instructed to direct their attention to the stimulus device 50, for example, a colored light from a light source attached to the testing device 100, such as a light-emitting diode (LED) or an audible stimulus from a speaker attached to the testing device 100. In some embodiments, the subject can direct and maintain their gaze at the stimulus device 50 if it is a visible stimulus. To measure the choice reaction time, the testing device 100 is released by the clinician and if the stimulus device 50, for example, having a LED on the testing device 100 illuminates in green contemporaneously as the device is released, the subject catches the device as quickly as possible using one kind of pinch grip: for example, using thumb and forefinger. If the LED illuminates in red, the subject catches the device as quickly as possible using another kind of pinch grip: for example, using thumb and third finger. At predetermined random time intervals, the clinician releases the device and the subject catches it as quickly as possible when the test condition is satisfied. In some embodiments one of more than two colors may be displayed; for example, one of up to four colors could be displayed calling for one of four pinch grips to be used comprised of using the thumb with one of the four fingers on the same hand. In some embodiments circuitry connected to stimulus device 50 can either randomize the color of the stimulus to be presented on each trial or present a pre-recorded sequence. For an electronic readout, the testing device 100 measures reaction time internally via an accelerometer and temporal recording device and displays the reaction time in milliseconds on a digital output screen. In some embodiments, the measurement device 60 can work in concert with microcontrollers 30 and 40 to determine and report the number (or percent) correct (incorrect) responses in a binary, 3-choice or more reaction time test.

In some embodiments the holding member 102 can be of sufficient width to allow its being caught by either the left hand or the right hand using a pinch grip. In a simple or recognition reaction time it can then be caught using either the left or the right hand, or both, as specified by the experimentor. But in a choice reaction time test if the LED lights green, the subject can be instructed to catch it with one hand. If the LED lights red, the subject can be instructed to catch it with the other hand. In some embodiments the subject will wear a glove with sensors on the digits that can be sensed by the member such that the device can "score" whether or not the correct digit closure pattern was used.

Applications for the Manual Neurological Testing Device

In some embodiments, the testing device 100 of the present disclosure can be used to determine a clinical measure of the recognition and/or choice reaction times of a subject. In some embodiments, the testing device 100 can be used to gather evidence of a sports-related concussion. A prolonged simple reaction time is a sign of sport-related concussion immediately following head trauma. A prolonged simple reaction time in the days following sport-related concussion can be a sub-clinical finding (i.e., is present when the athlete otherwise appears normal) indicating that complete recovery has not occurred; a prolonged simple reaction time places the athlete at increased risk for further injury. The reaction time data obtainable with the testing device 100s of the present disclosure provides objective data for the first time in the form of an inexpensive, yet accurate and intrinsically engaging, low-technology test. Furthermore, by subtracting the simple reaction time from the recognition reaction time one can calculate how much time the central nervous system required to perform the recognition process (between the Go-No Go and simple option). Likewise, subtracting the simple reaction time from the choice reaction time allows one to calculate how long the subject's central nervous system takes to make the choice between the two motor responses. Therefore being able to measure both simple and recognition reaction times, or simple and choice reaction times, with the same device gives the examiner a direct measure of central nervous system function that is not available with only simple, recognition or choice reaction time alone. The device's use would be indicated when an athlete has sustained head trauma and the diagnosis of concussion is in question, or after all clinical signs and symptoms of concussion have abated for an appropriate period of time in an athlete who has been diagnosed as having sustained a concussion, and the physician or athletic trainer is trying to decide whether the athlete should return to play. This decision currently involves subjective evaluation with few, if any, objective data (absent computerized neuropsychologic testing programs which are rarely available in the pediatric population).

The present disclosure provides a manual neurological testing device 100 that can be inexpensive and simple to use, relatively compact, e.g., no larger than a key fob, and to be able to measure simple reaction time and recognition reaction time and choice reaction time, forms of choice reaction time known to be impaired following concussion, and to confirm their relationship to the ability of the athlete to protect him- or herself during sport using a "sport-specific reaction time" (SPRT) measure.

In addition to the testing device 100 being an important diagnostic tool to determine in real time, the presence of some form of concussion, in a child, adolescent or adult, the testing device 100 can also be used as a screening device to determine whether a subject can return to a particular sport that may be physically demanding and probabilistic of a repeated neurological injury. Similarly, subjects undergoing medical treatment for a neurological condition may have their reaction time tested as a prognostic indicator whether or not a subject is able to return to some level of physical exposure. Subjects having overcome a neurological problem with medication may confirm recuperation by providing a reaction time result with the devices of the present disclosure that is indicative and correlates with neurological recovery. In one application, the post-concussion reaction time would have to equal the reaction time measured at the start of the playing season before a concussion was sustained, plus/minus a given margin of error. The preconcussion value of reaction time could be stored in the device memory and directly compared with the post-concussion value.

Other exemplary uses of the testing device 100 can include broader clinical applicability of the testing device 100 within the pediatric population and in adults. For example, it is well established that children with attention-deficit hyperactivity disorder (ADHD) have more prolonged and variable simple reaction time as compared to children without the disorder. Moreover, children with ADHD have diminished ability to stop an activity when cued as compared to other children, an ability that is restored with methylphenidate. The testing device 100 of the present disclosure also has application in assisting in the diagnosis of ADHD and monitoring response to therapy. Similarly, anti-epileptic drugs and anti-histamines have known effects on reaction time and are commonly used in the pediatric population; therefore the testing device 100 could be used with these children requiring these therapies to determine reaction time. In adults, the ability to accurately measure reaction time in the office setting would allow for the evaluation of patients with central neurologic disorders such as sleep apnea syndrome, traumatic brain injury, stroke, Parkinson's disease and dementia. In addition, the device could be used to monitor the effects of psychoactive medications commonly used such as neuroleptics, benzodiazepines, anti-epileptics, anti-depressants, hypnotics and opioids. The device could also be used to monitor function, and guide decisions regarding driving, return to work and fall risk in the setting of disease, polypharmacy and/or old age. Still further, the present teachings may find utility in connection with:

Central Neurological/Psychiatric Conditions, such as concussion/TBI, depression, dementia, distractions, stroke, ADHD (particularly monitoring response to medication), MS, psychologic stress, and Parkinson's Syndrome;

Peripheral Neurologic Conditions, such as polyneuropathy, demyelinating disease (AIDP, CIDP), myopathy, and diseases of neuromuscular junction (e.g., myasthenia gravis);

Metabolic Conditions, such as hyper/hypothyroid, renal failure/dialysis, menstrual cycle, hyper/hypocalcemia or hyper/hyponatremia, and hyper/hypoglycemia;

General Conditions, such as normal aging, OSA, sleep deprivation, alcohol intoxication, other drug effects, medication side effects, caffeine effects, exercise effects, pain effects, temperature effects, deconditioning, malnutrition, fever effects, and hypo/hypertension.

Moreover, the present teachings may find utility in connection with functional testing, such as in connection with sport protective response, driving, falls, occupational safety (machinery, etc), military protective response, fall protective response, and predicting athletic reaction time (e.g., track or swimming start).

EXAMPLES

Example 1

Manual Neurological Testing Device 100 with Digital Measurement Device

By way of example only and not for purposes of limitation, a testing device 100 as shown in FIGS. 3 and 5 includes an elongate holding member 102 similar to a wooden ruler having a biconcave shape measuring approximately 100 cm in length. The holding member 102 has a surface with ruler markings spaced in centimeters and millimeters. The holding member 102 has a roughened surface to prevent slippage between the holding member 102 and fingers when it is caught by the test subject. A weighted ballast 120 is attached to the lower end of the holding member 102 to help maintain the device in a vertical position prior to being released. Housed either within the holding member 102 or on the ballast are a spacer element, a linear accelerometer, two microcontroller chips, one or more light emitting diodes (LED), where one or both may have different colors, and a digital display screen as shown in FIGS. 2 and 4. The spacer maintains the subject's distal digits a fixed distance apart so they just do not touch the member prior to release. The linear accelerometer measures both onset and offset of motion of the member. The computer chip as shown in the inset of FIG. 2 is programmed to either a.) illuminate or fail to illuminate the bicolor LED at the onset of motion, or b.) illuminate the red LED or illuminate the green LED at the onset of motion. The microcontroller chip also records elapsed time (in milliseconds) from onset of motion to arrest of motion and outputs this information to the digital output screen shown in the inset of FIG. 2.

A first microcontroller initializes all I/O ports and timer and then checks the test mode (simple reaction time or "Go-No Go"). Then the first microcontroller measures the onset of the acceleration when the stick is dropped by the clinician. When the acceleration exceeds a set threshold, the circuit turns on one color in the bicolor LED and sends a signal to a second microcontroller to start the clock. If the stick experiences a sudden acceleration change, such as being slowed or halted by the fingers or striking the ground, then the first microcontroller sends a signal to the second microcontroller to stop the clock. (The second microcontroller initializes the LCD module and waits for a signal from the first microcontroller to start or stop the clock.) The testing device 100 has a unit which displays the reaction time on a display unit (screen) which is the calculated time between the onset and offset of acceleration of the testing device 100 and therefore the measured reaction time. The LED can be bicolored, having a green and a red LED in one module.

It should be appreciated that in some embodiments, the measurement and display of response accuracy in the measurement of Recognition Reaction Time and Choice Reaction Time can be provided. In the case of Recognition Reaction Time, it can be incorporated into circuitry 60 and apparatus described herein. In the case of a binary (two-choice) Choice Reaction Time, the present teachings can comprise one or more (such as two) thimble or other sensor disposed on a finger that is capable of detecting when the finger touches the "handle" and the other does not. A touch could be indicated by a pressure-sensitive switch or pressure sensor or proximity sensor. In some embodiments, such as a three-choice Choice Reaction Time system, the thimble or other sensor can be placed on three finger tips. Response accuracy would be calculated for the RRT as the number of correct responses versus the total number of responses, the number of incorrect responses versus the total number of responses, and/or the total number of correct responses versus the total number of incorrect responses. In some embodiments, the response accuracy for the binary (2-choice) Choice Reaction Time could be calculated as the 'number of correct responses for Choice 1' versus the 'total number of trials with Choice 1', and the 'number of correct responses for Choice 2' versus 'total number of trials with Choice 2', and so on for additional choices.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A manual neurological testing device for measuring a human subject's reaction time comprising:
   a) a releasable holding member operable to be released by a human tester and free fall in response to the force of gravity and be subsequently grasped by the human subject;
   b) a stimulus device fixedly coupled with said releasable holding member so as to free fall therewith in response to the force of gravity, said stimulus device operable to output a perceivable stimulus in response to free fall; and
   c) a measurement device fixedly coupled with said releasable holding member so as to free fall therewith in response to the force of gravity, said measurement device operable to measure the human subject's reaction time for grasping said releasable holding member as said releasable holding member, said stimulus device, and said measurement device collectively free fall relative to said perceivable stimulus.

2. The manual neurological testing device according to claim 1 wherein said releasable holding member is a rigid member.

3. The manual neurological testing device according to claim 1 wherein said releasable holding member is a flexible member.

4. The manual neurological testing device according to claim 1 wherein said releasable holding member is a telescoping member.

5. The manual neurological testing device according to claim 1 wherein said measurement device operable to determine a recognition reaction time response accuracy.

6. The manual neurological testing device according to claim 1 wherein said measurement device comprises an accelerometer operable to detect acceleration of at least one of said releasable holding member and said measurement device.

7. The manual neurological testing device according to claim 1 wherein said stimulus device comprises a visual cue device.

8. The manual neurological testing device according to claim 1 wherein said stimulus device comprises an audible cue device.

9. The manual neurological testing device according to claim 1 wherein said stimulus device operable to output a plurality of distinct cues for eliciting a corresponding unique response by the subject.

10. The manual neurological testing device according to claim 1 wherein said stimulus device operable to output a plurality of distinct cues for eliciting a corresponding unique response by the subject, a first of said plurality of cues indicating a catch command to the subject, a second of said plurality of cues indicating a no-catch command to the subject.

11. The manual neurological testing device according to claim 1, further comprising:
    a spacer system for positioning the subject's appendage in a pre-test position.

12. The manual neurological testing device according to claim 1, further comprising:
    a spacer system for positioning the subject's appendage in a pre-test position, said spacer system having a proximity sensor operable to detect positioning of the subject's appendage.

13. The manual neurological testing device according to claim 1, further comprising:
    a spacer system for positioning the subject's appendage in a pre-test position, said spacer system having a body defining a predetermined dimension for positioning of the subject's appendage.

14. The manual neurological testing device according to claim 1 wherein said stimulus device operable to output a perceivable stimulus comprises said stimulus device outputting a perceivable stimulus in response to detection of said free fall of said releasable holding member.

15. A manual neurological testing device for measuring a subject's reaction time comprising:
    a) a releasable holding member configured to free fall and then subsequently be grasped by the subject;
    b) a control module coupled with said releasable holding member for free fall therewith, said control module comprising:
       i) a displacement sensor operable to determine a predetermined onset and an offset of free fall motion of said releasable holding member in a vertical direction during free fall, said offset of free fall motion occurring when said releasable holding member and said control module collectively free fall and are then grasped by the subject;
       ii) a controller connected to said displacement sensor, said controller comprising: a stimulus driving output and a timer on/off output; and
       iii) a timing device in communication with said timer on/off output, said timing device operable to measure a period of time elapsed between said predetermined onset and said offset of motion of said releasable holding member and operable to send said period of time elapsed to said controller; and
    c) a stimulus device coupled with said releasable holding member for free fall therewith to be perceived by the subject, said stimulus device in electronic communication with said controller and operable to output a stimulus in response to said stimulus driving output upon detection of said onset of free fall motion of said releasable holding member, said control module, and said stimulus device.

16. A method for manually measuring the reaction time in a subject, the method comprising:
   (a) positioning a manual neurological testing device operable to measure the reaction time of the subject, said manual neurological testing device having a releasable holding member operable to free fall and then be grasped by the subject; a stimulus device coupled with said releasable holding member to free fall simultaneously therewith, said stimulus device outputting a perceivable stimulus; and a measurement device coupled with said releasable holding member and said stimulus device to free fall simultaneously therewith;
   (b) releasing said releasable holding member, said stimulus device, and said measurement device collectively in free fall with or without said perceivable stimulus; and
   (c) determining the time taken for the subject to grasp said releasable holding member during free fall after releasing said releasable holding member, said stimulus device, and said measurement device collectively.

17. The method according to claim 16 wherein said determining the time taken for the subject to grasp said releasable holding member comprises determining the time taken for the subject to grasp said releasable holding member using a plurality of sensors disposed on the subjects fingers.

* * * * *